US010426827B1

(12) United States Patent
Deisseroth

(10) Patent No.: US 10,426,827 B1
(45) Date of Patent: Oct. 1, 2019

(54) DENGUE HEMORRHAGIC FEVER VIRUS VACCINE

(71) Applicant: MicroVAX, LLC, Manassas, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 140 days.

(21) Appl. No.: 14/724,409

(22) Filed: May 28, 2015

Related U.S. Application Data

(63) Continuation-in-part of application No. 14/067,523, filed on Oct. 30, 2013, now abandoned, which is a continuation-in-part of application No. 11/593,458, filed on Nov. 6, 2006, now Pat. No. 9,533,036.

(60) Provisional application No. 61/725,535, filed on Nov. 13, 2012.

(51) Int. Cl.
*A61K 39/12* (2006.01)
*A61K 39/00* (2006.01)

(52) U.S. Cl.
CPC .......... *A61K 39/12* (2013.01); *A61K 2039/53* (2013.01); *A61K 2039/54* (2013.01)

(58) Field of Classification Search
CPC ................ A61K 2039/53; A61K 39/00; A61K 2039/55516; A61K 39/0011; C07K 14/47
See application file for complete search history.

(56) References Cited

U.S. PATENT DOCUMENTS

| | | | | |
|---|---|---|---|---|
| 2007/0128223 A1* | 6/2007 | Tang | ..................... | A61K 39/145 |
| | | | | 424/209.1 |
| 2007/0269456 A1* | 11/2007 | Lasher | ................... | A61K 39/21 |
| | | | | 424/208.1 |
| 2010/0291144 A1* | 11/2010 | Ramanathan | .......... | A61K 39/12 |
| | | | | 424/208.1 |

FOREIGN PATENT DOCUMENTS

WO  WO2005000235  *  1/2005

OTHER PUBLICATIONS

Wan et al., "Current progress in dengue vaccines", 2013, Journal of Biomedical Science, 20(37):1-9.*
Oyston et al., "The current challenges for vaccine development", 2012, Journal of Medical Microbiology, 61:889-894.*
Sukupolvi-Petty et al., Journal of Virology, 2007, vol. 81, No. 23, pp. 12816-12826.*
Neefjes et al., Towards a systems understanding of MHC class I and MHC class II antigen presentation, 2011, Nature Reviews: Immunology, vol. 11.*
D. Gubler, *Epidemic dengue/dengue hemorrhagic fever as a public health, social and economic problem in the $21^{st}$ century*, Trends in Microbiology, vol. 10, No. 2; Feb. 2002, pp. 100-103.

World Health Organization, *Dengue: Guidelines for Diagnosis, Treatment, Prevention and Control*, WHO New Edition 2009, Geneva, 160 pages. http://whglibdoc.who.int/pubilcations/2009/9789241547871_eng.pdf.
D. Gubler, *The Economic Burden of Dengue*, The American Society of Tropical Medicine and Hygiene, 86(5), 2012, pp. 743-744.
M. Beatty et al., *Best Practices in Dengue Surveillance: A Report from the Asia-Pacific and Americas Dengue Prevention Boards*, Asia-Pacific and Americas Dengue Prevention Boards Surveillance Working Group, PLoS Negl Trop Dis 4(11): e890, Nov. 2010; p. 1-7.
S. Whitehead et al., *Prospects for a dengue virus vaccine*, Nature Reviews Microbiology, vol. 5, Jul. 2007; pp. 518-528.
R. Zellweger et al., *Antibodies enhance infection of LSECs in a model of ADE-induced severe dengue disease*, Cell Host Microbe, Feb. 18, 2010; 7(2); pp. 1-20.
S. Balsitis et al., *Lethal Antibody Enhancement of Dengue Disease in Mice Is Prevented by Fc Modification*, PLoS Pathogens, Feb. 2010, vol. 6, Issue 2; pp. 1-13.
M. Beltramello et al., *The Human Immune Response to Dengue Virus Is Dominated by Highly Cross-Reactive Antibodies Endowed with Neutralizing and Enhancing Activity*, Cell Host Microbe, Sep. 16, 2010; 8(3), pp. 1-25.
C. Simmons et al., *Dengue*, New England Journal of Medicine 366;15, Apr. 12, 2012, pp. 1423-1432.
B. Coller et al., *Dengue vaccines: progress and challenges*, Current Opinion in Immunology, 2011; 23: pp. 391-398.
S. Halstead, *Dengue*, Lancet; vol. 370, Nov. 10, 2007; pp. 1644-1652.
J. Bixler, *Florida confirms 24 cases of dengue fever in Key West*, CNN, Aug. 3, 2010, p. 1-2.
H. Chen et al., *Both Virus and Tumor Necrosis Factor Alpha Are Critical for Endothelium Damage in a Mouse Model of Dengue Virus-Induced Hemorrhage*, Journal of Virology, Jun. 2007, vol. 81, No. 11; pp. 5518-5526.
M. Cassetti et al., *Report of an NIAID Workshop on Dengue Animal Models*, Vaccine, Jun. 11, 2010, 28(26), pp. 1-12.
M. Bray et al., *Monkeys Immunized with Intertypic Chimeric Dengue Viruses Are Protected against Wild-Type Virus Challenge*, Journal of Virology, Jun. 1996, vol. 70, No. 6; pp. 4162-4166.
L. Yauch et al., *Mouse models of dengue virus infection and disease*, Antiviral Research, Nov. 2008, 80(2); pp. 1-14.
S. Halstead, *Dengue vaccine development: a 75% solution?*, Lancet, vol. 380, Sep. 11, 2012; pp. 1535-1536.
A. Sabchareon et al., *Protective efficacy of the recombinant, live-attenuated, CYD tetravalent dengue vaccine in Thai schoolchildren: a randomised, controlled phase 2b trial*, Lancet, vol. 380, Sep. 11, 2012; pp. 1559-1567.

(Continued)

*Primary Examiner* — Benjamin P Blumel
(74) *Attorney, Agent, or Firm* — Jacob Frank; Glenn Snyder; Snyder, Clark, Lesch & Chung, LLP

(57) ABSTRACT

Provided are methods of selecting domains of the dengue hemorrhagic fever virus E protein for generating a neutralizing antibody immune response to the dengue hemorrhagic fever virus. The method comprises priming an individual by administering a mixture of expression vectors encoding fusion proteins or the fusion proteins themselves which comprises the DHFV E antigen fragment linked to the extracellular domain of the CD40 ligand. The expression vector comprises a transcription unit encoding a secretable fusion protein, the fusion protein containing the DHFV E antigen fragment linked to the CD40 ligand. The methods may be used to immunize an individual against all four strains of dengue hemorrhagic fever virus.

4 Claims, No Drawings
Specification includes a Sequence Listing.

(56) References Cited

OTHER PUBLICATIONS

T. Jefferson et al., *Efficacy and effectiveness of influenza vaccines in elderly people: a systematic review*, Lancet, vol. 366, Sep. 22, 2005; pp. 1165-1174.
K. Goodwin et al., *Antibody response to influenza vaccination in the elderly: A quantitative review*, Vaccine 24 (2006); pp. 1159-1169.
M. Jackson et al., *Influenza vaccination and risk of community-acquired pneumonia in immunocompetent elderly people: a population-based, nested case-control study*, Lancet, vol. 372, Aug. 2, 2008; pp. 398-405.
L. Simonsen et al., *Mortality benefits of influenza vaccination in elderly people: an ongoing controversy*, Lancet Infect Dis, vol. 7; 2007, pp. 658-666.
L. Dong et al., *An immunostimulatory oligodeoxynucleotide containing a cytidine-guanosine motif protects senescence-accelerated mice from lethal influenza virus by augmenting the T helper type 1 response*, Journal of General Virology (2003), 84, pp. 1623-1628.
S. Eaton et al., *Age-related Defects in CD4 T Cell Cognate Helper Function Lead to Reductions in Humoral Responses*, Journal of Experimental Medicine, vol. 200, No. 12, Dec. 20, 2004; pp. 1613-1622.
L. Zhang et al., *An adenoviral vector cancer vaccine that delivers a tumor-associated antigen/CD40-ligand fusion protein to dendritic cells*, PNAS, Dec. 9, 2003, vol. 100, No. 25; pp. 15101-15106.
H. Akbulut et al., *Vector Targeting Makes 5-Fluorouracil Chemotherapy Less Toxic and More Effective in Animal Models of Epithelial Neoplasms*, Clinical Cancer Research, vol. 10, Nov. 15, 2004; pp. 7738-7746.
Y. Tang et al., *Multistep process through which adenoviral vector vaccine overcomes anergy to tumor-associated antigens*, Blood, Nov. 1, 2004, vol. 104, No. 9; pp. 2704-2713.
H. Akbulut et al., *Antitumor immune response induced by i.t. injection of vector-activated dendritic cells and chemotherapy suppresses metastatic breast cancer*, Mol Cancer Ther 2006; 5(8), Aug. 2006; pp. 1975-1985.
Y. Tang et al., *Vector Prime/Protein Boost Vaccine That Overcomes Defects Acquired during Aging and Cancer*, The Journal of Immunology, 2006, 177: pp. 5697-5707.
Y. Tang et al., *Vaccine strategies for cancer and infectious diseases in the elderly*, Gene Therapy 2007, pp. 2-11.
H. Akbulut et al., *Chemotherapy Targeted to Cancer Tissue Potentiates Antigen-specific Immune Response Induced by Vaccine for In Vivo Antigen Loading and Activation of Dendritic Cells*, Molecular Therapy, vol. 16; No. 10, Oct. 2008; pp. 1753-1760.
Y. Tang, *Use of CD40L immunoconjugates to overcome the defective immune response to vaccines for infections and cancer in the aged*, Cancer Immunology Immunotherapy (2009) 58; pp. 1949-1957.
T. Han et al., *Vector prime protein boost vaccination in the setting of myeloablative-induced lymphopenia suppresses growth of leukemia and solid tumors*, Bone Marrow Transplatation (2010) 45; pp. 550-557.
H. Akbulut et al., *Addition of adenoviral vector targeting of chemotherapy to the MUC-1/ecdCD40L VPPP vector prime protein boost vaccine prolongs survival of mice carrying growing subcutaneous deposits of Lewis lung cancer cells*, Gene Therapy (2010), p. 1-8.
A. Deisseroth et al., *TAA/ecdCD40L adenoviral prime-protein boost vaccine for cancer and infectious diseases*, Cancer Gene Therapy (2012), p. 1-5.
WMPB Wahala et al., *Dengue virus neutralization by human immune sera: role of envelope protein domain III—reactive antibody*, Virology, Sep. 15, 2009; 392(1): pp. 1-23.
W. Crill et al., *Monoclonal Antibodies That Bind to Domain III of Dengue Virus E Glycoprotein Are the Most Efficient Blockers of Virus Adsorption to Vero Cells*, Journal of Virology, Aug. 2001, vol. 75, No. 16, p. 7769-7773.
J. Roehrig et al., *Monoclonal Antibody Mapping of the Envelope Glycoprotein of the Dengue 2 Virus, Jamaica*, Virology 246, pp. 317-328 (1998).
Soila Sukupolvi-Petty et al., *Type- and Subcomplex-Specific Neutralizing Antibodies against Domain III of Dengue Virus Type 2 Envelope Protein Recognize Adjacent Epitopes*, Journal of Virology, Dec. 2007, p. 12816-12826.
Daniela Weiskopf et al., *Comprehensive analysis of dengue virus-specific responses supports an HLA-linked protective role for CD8+ T cells*, PNAS Early Edition, pp. 1-8, Mar. 19, 2013.
Lauren E. Yauch et al., *A Protective Role for Dengue Virus-Specific CD8+ T Cells*, The Journal of Immunology, 10 pages, vol. 182, pp. 4865-4873, 2009.
Sinu Paul et al., *HLA Class I Alleles Are Associated with Peptide-Binding Repertoires of Different Size, Affinity, and Immunogenicity*, The Journal of Immunology, vol. 191, pp. 1-9, Nov. 2013.

\* cited by examiner

```
                          SEQUENCE LISTING

<160> NUMBER OF SEQ ID NOS: 12

<210> SEQ ID NO 1
<211> LENGTH: 27
<212> TYPE: PRT
<213> ORGANISM: Artificial Sequence
<220> FEATURE:
<223> OTHER INFORMATION: Synthetic Construct

<400> SEQUENCE: 1

Leu Lys Gly Met Ser Tyr Val Met Cys Thr Gly Ser Phe Lys Leu Glu
1               5                   10                  15

Lys Glu Val Ala Glu Thr Gln His Gly Thr Val
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Leu Lys Gly Met Ser Tyr Ser Met Cys Thr Gly Lys Phe Lys Val Val
1               5                   10                  15

Lys Glu Ile Ala Glu Thr Gln His Gly Thr Ile
            20                  25
```

```
<210> SEQ ID NO 3
<211> LENGTH: 27
<212> TYPE: PRT
<213> ORGANISM: Artificial Sequence
<220> FEATURE:
<223> OTHER INFORMATION: Synthetic Construct

<400> SEQUENCE: 3

Leu Lys Gly Met Ser Tyr Ala Met Cys Leu Ser Ser Phe Val Leu Lys
1               5                   10                  15

Lys Glu Val Ser Glu Thr Gln His Gly Thr Ile
            20                  25

<210> SEQ ID NO 4
<211> LENGTH: 27
<212> TYPE: PRT
<213> ORGANISM: Artificial Sequence
<220> FEATURE:
<223> OTHER INFORMATION: Sythetic Construct

<400> SEQUENCE: 4

Ile Lys Gly Met Ser Tyr Thr Met Cys Ser Gly Lys Phe Ser Ile Asp
1               5                   10                  15

Lys Glu Met Ala Glu Thr Gln His Gly Thr Thr
            20                  25

<210> SEQ ID NO 5
<211> LENGTH: 34
<212> TYPE: PRT
<213> ORGANISM: Artificial Sequence
<220> FEATURE:
<223> OTHER INFORMATION: Synthetic Construct

<400> SEQUENCE: 5

Leu Val Gln Val Lys Tyr Glu Gly Thr Asp Ala Pro Cys Lys Ile Pro
1               5                   10                  15

Phe Ser Thr Gln Asp Glu Lys Gly Ala Thr Gln Met Gly Arg Leu Ile
            20                  25                  30

Thr Ala

<210> SEQ ID NO 6
<211> LENGTH: 34
<212> TYPE: PRT
<213> ORGANISM: Artificial Sequence
<220> FEATURE:
<223> OTHER INFORMATION: Synthetic Construct

<400> SEQUENCE: 6

Val Ile Arg Val Gln Tyr Glu Gly Thr Gly Ser Pro Cys Lys Ile Pro
1               5                   10                  15

Phe Glu Ile Met Asp Leu Glu Lys Arg His Val Leu Gly Arg Leu Ile
            20                  25                  30

Thr Val

<210> SEQ ID NO 7
<211> LENGTH: 34
<212> TYPE: PRT
<213> ORGANISM: Artificial Sequence
<220> FEATURE:
<223> OTHER INFORMATION: Synthetic Construct
```

```
<400> SEQUENCE: 7

Leu Ile Lys Val Glu Tyr Lys Gly Glu Asp Ala Pro Cys Lys Ile Pro
1               5                   10                  15

Phe Ser Thr Glu Asp Gly Gln Gly Lys Ala His Asn Gly Arg Leu Ile
            20                  25                  30

Thr Ala

<210> SEQ ID NO 8
<211> LENGTH: 34
<212> TYPE: PRT
<213> ORGANISM: Artificial Sequence
<220> FEATURE:
<223> OTHER INFORMATION: Synthetic Construct

<400> SEQUENCE: 8

Val Val Lys Val Lys Tyr Glu Gly Ala Gly Ala Pro Cys Lys Val Pro
1               5                   10                  15

Ile Glu Ile Arg Asp Val Asn Lys Gly Lys Val Val Gly Arg Ile Ile
            20                  25                  30

Ser Ser

<210> SEQ ID NO 9
<211> LENGTH: 40
<212> TYPE: PRT
<213> ORGANISM: Artificial Sequence
<220> FEATURE:
<223> OTHER INFORMATION: Synthetic Construct

<400> SEQUENCE: 9

Asn Pro Ile Val Thr Asp Lys Glu Lys Pro Val Asn Ile Glu Ala Glu
1               5                   10                  15

Pro Pro Phe Gly Glu Ser Tyr Ile Val Val Gly Ala Gly Glu Lys Ala
            20                  25                  30

Leu Lys Leu Ser Trp Phe Lys Lys
        35                  40

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct

<400> SEQUENCE: 10

Asn Pro Ile Val Thr Glu Lys Asp Ser Pro Val Asn Ile Glu Ala Glu
1               5                   10                  15

Pro Pro Phe Gly Asp Ser Tyr Ile Ile Ile Gly Val Glu Pro Gly Gln
            20                  25                  30

Leu Lys Asn Trp Phe Lys Lys
        35

<210> SEQ ID NO 11
<211> LENGTH: 40
<212> TYPE: PRT
<213> ORGANISM: Artificial Sequence
<220> FEATURE:
<223> OTHER INFORMATION: Synthetic Construct
```

```
<400> SEQUENCE: 11

Asn Pro Val Val Thr Lys Lys Glu Glu Pro Val Asn Ile Glu Ala Glu
1               5                   10                  15

Pro Pro Phe Gly Glu Ser Asn Ile Val Ile Gly Ile Gly Asp Lys Ala
            20                  25                  30

Leu Lys Ile Asn Trp Tyr Lys Lys
        35                  40

<210> SEQ ID NO 12
<211> LENGTH: 40
<212> TYPE: PRT
<213> ORGANISM: Artificial Sequence
<220> FEATURE:
<223> OTHER INFORMATION: Synthetic Construct

<400> SEQUENCE: 12

Thr Pro Leu Ala Glu Asn Thr Asn Ser Ala Thr Asn Ile Glu Leu Glu
1               5                   10                  15

Pro Pro Phe Gly Asp Ser Tyr Ile Val Ile Gly Val Gly Asn Ser Ala
            20                  25                  30

Leu Thr Leu His Trp Phe Arg Lys
        35                  40
```

DENGUE HEMORRHAGIC FEVER VIRUS VACCINE

CROSS-REFERENCE TO RELATED APPLICATIONS

This application is a continuation-in-part of U.S. application Ser. No. 14/067,523 filed on Oct. 30, 2013, which in turn is a continuation-in-part of application Ser. No. 11/593,458, filed on Nov. 6, 2006 which, including all figures and tables, are both incorporated herein by reference in their entireties. This application claims priority and the benefit under 35 U.S.C. § 119(e) of U.S. Provisional Patent Application Ser. No. 61/725,535, filed on Nov. 13, 2012, which, including all figures and tables, is incorporated herein by reference in its entirety. This application also relates to U.S. patent application Ser. No. 14/058,526, filed Oct. 21, 2013 which, including all its figures and tables, is incorporated herein by reference.

FIELD OF THE INVENTION

The present invention relates to a dengue hemorrhagic fever virus vaccine and compositions thereof and methods of developing the vaccine, to generate an immunity against infection by dengue hemorrhagic fever viruses.

The following discussion of the background of the invention is merely provided to aid the reader in understanding the invention and is not admitted to describe or constitute prior art to the present invention.

Dengue Hemorrhagic Fever Virus (DHFV) is known as "break-bone fever" and is a positive strand RNA virus transmitted by mosquitoes in human subjects (1). It was recently observed to have increased in incidence in many parts of the world in which there are sub-tropical or tropical climates which support the prevalence of the arthropod vector (1). It is estimated that 50 to 100 million dengue infections occur each year (2-4). Thus, Dengue has emerged as a significant global health threat.

There are four major DHFV strains, and survival following the occurrence of the first DHFV infection is associated against life-long immunity against that infecting DHFV strain, but not to the other three heterologous strains (5). The neutralizing antibody immune response to the antigens of the DHFV strain that is the first to infect, is strong. In contrast, the neutralizing antibody response to the other three heterologous strains which cause an infection subsequent to the first strain is weak. These heterologous antibodies disappear within a matter of weeks after the infection. The weakness of this heterologous immune response means that it is not fully protective to three of the four strains (5). Importantly, the disappearance of the neutralizing antibodies to heterologous antigens has been associated with increased susceptibility to infection by the heterologous strains and to the development of DSS (6-8).

The initial event in an infection is inoculation of the virus into the skin by mosquitoes, followed by replication of the virus in dendritic cells (DCs), lymphocytes and monocytes, and then the entry of the virus into the bloodstream at high titers of one million infectious units/ml of blood which leads to seeding of visceral organs (5). This initial period of infection is often characterized by the sudden onset of high fever and rash with severe pain behind the eyes, joints, muscles and bone (which have led to the common name for DHFV infections: "break-bone fever") for 3-7 days, accompanied by flushing of the face and chest, petechia, clinically significant bleeding, myalgias, headache, vomiting and diarrhea, elevated serum levels of transaminases, thrombocytopenia, and lymphopenia.

Most often, after 3-7 days, the fever abates and the patient is left with long lasting immunity (due to high neutralizing antibody titers) against the infecting strain of DHFV. There is also short lived protection against the other three strains of DHFV due to a transient production of cross-strain neutralizing antibodies, but these cross-reactive neutralizing antibodies are low level and disappear after 3-4 months (5).

In some patients, at the time of resolution of the fever, this initial period is followed by a sudden and rapidly evolving syndrome of bleeding, edema, hypotension, systemic vascular collapse and death within 24 hours due to a capillary leak syndrome, and occasionally fulminant hepatic failure (9-10). This is called the Dengue Shock Syndrome (DSS). Halstead et al. (11) speculates, that DSS occurs in the setting of a secondary infection with a DHFV strain that is different from a previous infection with DHFV that was associated with a different serotype. Because this is a disease transmitted by mosquitoes, this disease worldwide affects populations of children in tropical and subtropical countries (3-4). DHFV infections have been reported in Florida in 2009 (12). There is no treatment for DHFV infections except for supportive care, and up to now, there is no effective vaccine that protects against all four viral strains.

The clinical features described above have been attributed to an immunological mechanism, which occurs in individuals who have experienced a previous infection with a different strain of DHFV. This phenomenon has been referred to as "antibody-dependent enhancement" (6-8). This may lead to the development of DSS in individuals with incomplete and transient immune protection against heterologous DHFV strains following a previous mild infection of the first DHFV strain to infect, or to the administration of an unsuccessful vaccination. This condition, in which the infection of an individual with a single strain of DHFV, can lead to blocking of the immune response to an infection with a second strain (6-8). Some experts speculate that this antibody enhancement leads to the more serious form of DHFV infection that results in vascular collapse, shock and death (6-8). This phenomenon, that of increased susceptibility to infection with a second strain of DHF virus, once a weak response to the first DHF virus strain specific vaccination has occurred, has been reported for DHFV (6-8).

Vaccine development for DHFV has been hampered by the poor replication of human isolates of DHFV in immunocompetent mice (13). Mouse models to study DHFV in which immunodeficient mice with defective interferon response are reconstituted with an immune response system, have been only modestly successful (13-16). Study of vaccine strategies in non-human primates (15) and swine have been tried as well (14), also with only limited success. Thus, the public health measures have focused on the control of the mosquito populations which carry the disease.

Recently, Sanofi reported (17) the partial failure of its new attenuated viral vaccine strategy for DHFV to protect vaccinated individuals against all four strains of DHFV (18). This has been reported as a major setback for the field. In this trial, which was reported in the article published in the Lancet (17), the efficacy was said to be 30%. This vaccine was based on an attenuated strain of yellow fever virus which contains DHFV antigens characteristic of the four major DHFR strains. Patients received vaccination at 0, 6 and 12 months with each of four strains, each one specific for a different strain of DHFV. Patients (>4000) were randomized 2:1 to receive the DHFV/yellow fever chimeric attenuated vaccine or a control vaccine. The incidence of the mild infection against DHFV strain 2 was not different in the two arms (no protective effect of the vaccine), and a moderate decrease in the treatment arm versus the control of cases of DHFV strain 1 (poor response). In contrast, there was 80-90% protection against DHFV strains 3 and 4 with the DHFV/yellow fever chimeric attenuated vaccine. The explanation for the incomplete protection against DHFV strain 2 and the partial protection against strain 1 was that the various strains of DHFV/yellow fever virus vaccines generated different titers in the vaccinated individuals and the strains with the low titers generated only low levels of neutralizing antibody response against the proteins from DHFV strains 1 and 2 (18).

Many factors can reduce the response of an individual to a viral infection or to the induction of an immune response to vaccination: chronic disease, chronic infection, cancer and advanced chronological age. Additional problems include: weak immunogenicity of the target antigen, qualitative or quantitative defects of CD4 helper T cells, defective response in the older aged population due to diminished expression of CD40L in activated CD4 helper T cells, or low levels of presentation of target antigens on Class I or II MHC in dendritic cells (DCs). Among individuals above the age of 55, less than 20% of individuals vaccinated with the yearly multi-valent particle inactivated influenza vaccine develop a fully positive immune response (19-22).

One explanation for this reduced response is the decrease in function of the immune system with age. For example, there is a decrease in the number of naïve, antigen unexposed CD4 and CD8 T cells. Additionally, the ratio of the naïve to memory CD8/CD4 cells decreases as the chronological age increases. Further, CD4 cells become impaired, acquiring both quantitative and functional defects, such as diminished levels of the CD40 ligand (CD40L) on the surface of CD4 cells as well as a temporal retardation of the rate at which CD40 ligand (CD40L) is expressed on the surface of the CD4 cells following activation. (23-24). Accordingly, the amount of antibody that an elderly individual is able to generate will be lower following infection or conventional vaccination. The CD40L is important for the expansion of antigen specific CD8 effector T cells and antigen specific B cells in response to vaccination.

SUMMARY OF THE INVENTION

Vaccines have been described that include an expression vector encoding a fusion protein that includes an antigen fused to CD40 ligand (25-35). See, e.g., U.S. Patent Application Publication US 2005-0226888 (U.S. patent application Ser. No. 11/009,533) titled "Methods for Generating Immunity to Antigen," filed Dec. 10, 2004. Also see, for example, publication WO/2007/056266, publication date May 18, 2007, International filing date Nov. 6, 2006, entitled "CD40 Ligand Fusion Protein Vaccine".

The present invention provides new vaccines for protecting against infection by dengue hemorrhagic fever virus ("DHFV"). An immune response to fragments of the dengue protein E is achieved by attaching inframe a series of epitopes from the E protein from each of the four DHFV strains to the ecdCD40L, to create a vaccine for all the major strains of the DHFV. Because the infection by an initial DHFV strain generates only short lived neutralizing antibodies that protect against heterologous strains, and the infection with an initial strain may sensitize an individual to more severe infectious with heterologous strains (5-8), it would be of advantage to immunize against all four strains simultaneously. In order to accomplish this, Applicant chose to use 3 fragments of domains III of the E antigen from all 4 strains of the DHFV to attach to the ecdCD40L, for an E/ecdCD40L DHFV vaccine.

The E protein of DHFV was selected for the target of our vaccine since in the flavivirus group, to which DHFV belongs, the E protein is one of the major targets for neutralizing antibodies (5, 36-37). The E protein is therefore thought to be necessary for attachment of the virus to host cells, and for the low pH fusion of the host cell membranes with the virus which is necessary for viral entry (36). The E protein has three domains:

Domain I: This region is thought to be the hinge between Domains II and III. Domain I contains primarily epitopes that elicit non-neutralizing antibodies (37).

Domain II: This domain is involved in virus mediated membrane fusion and contains epitopes which elicit both neutralizing as well as non-neutralizing antibodies (37).

Domain III: This domain which is approximately 100 amino acids long in each of the four strains, is thought to contain the host binding antireceptor which is necessary for initial attachment of the virus to the cell membrane (37). The epitopes in Domain III elicit only neutralizing antibodies and therefore has been chosen as the target domain for vaccine development (37).

Domain III is the preferred target in the E protein as compared to Domains I and II because:
  a. Domains I and II have epitopes which elicit non-neutralizing antibodies whereas all of the epitopes within Domain III induce neutralizing antibodies (37);
  b. Domain III mediates the first step of infection of host cells by the virus: that of attachment of the virus by cellular receptors (37). Thus, if that step is blocked by induction of neutralizing antibodies to Domain III, total protection will be produced.
  c. The above stated properties in (a) and (b), of the E protein are shared by each of the four strains.

In order to circumvent functional defects in the immune response (19-24), as well as increase the immunogenicity of the target associated antigens, Applicant's laboratory (25-35) designed the TAA/ecdCD40L vaccine strategy. There are four versions of this vaccine: 1. One in which the TAA/ecdCD40L transcription unit is embedded in a replication incompetent adenoviral vector (Ad-sig-TAA/ecdCD40L) which is then injected SC three times at seven day intervals; 2. One in which the TAA/ecdCd40L transcription unit is embedded in a replication incompetent adenoviral vector (Ad-sig-TAA/ecdCD40L) which is used as an initial priming injection, followed by two sc injections of the TAA/ecdCD40L protein; 3. One in which the vaccine consists solely of the TAA/ecdCD40L protein; and, 4. One in which the TAA/ecdCD40L is inserted into a plasmid DNA expression vector. The TAA is connected through a linker to the extracellular domain (ecd) of the potent immunostimulatory signal CD40 ligand (CD40L).

The attachment of such DHFV TAA to the CD40L accomplishes two things: the binding of the TAA/ecdCD40L protein to the CD40 receptor on the DCs as well as on the B cells and T cells, activate these cells thereby promoting a potent immune response (25, 27, 29); 2. once the TAA/ecdCD40L protein is engaged on the CD40 receptor of the DC, the entire TAA/ecdCD40L protein is internalized into the DC in a way that allows Class I as well as Class II MHC presentation (25).

The activated TAA loaded DCs then migrate to the regional lymph nodes (27, 29) where they can activate and induce expansion of the TAA specific $CD8^+$ effector T cells.

These antigen specific $CD8^+$ effector cells become increased in number in the lymph nodes (27, 29), and egress from the lymph nodes into the peripheral blood. The antigen specific CD8 effector T cells exit the intravascular compartment and enter into the extra-vascular the sites of inflammation or infection (29). In addition to showing that this vaccine increases the antigen specific $CD8^+$ effector T cells in the sites of inflammation (29), Applicant's laboratory has shown that the activation and expansion of the B cells by the TAA/ecdCD40L protein increases the levels of the TAA specific antibodies in the serum (29, 32, 33).

DETAILED DESCRIPTION OF THE INVENTION

As used herein an "antigen" is any foreign material that is specifically bound by the combining site of an antibody or by the combining site of a T cell antigen receptor. Antigens may also be immunogens if they are able to trigger an immune response, or haptens if not.

As used herein, "antigenic determinant" refers to a single antigenic site or epitope on a complex antigenic molecule or particle. a minimal portion of a molecule that interacts with an antibody or T cell receptor. Antigenic determinants may be linear or discontinuous.

In one approach, the sequence encoding the DHFV antigen in the fusion protein transcription unit is 5' to sequence encoding the CD40 ligand. In another approach, the sequence encoding the CD40 ligand in the fusion protein transcription unit is 5' to sequence encoding the DHFV antigen. In a preferred embodiment, the CD40 ligand lacks all or a portion of its transmembrane domain.

In another aspect, the invention provides methods of immunizing an individual against infection by DHFV. The method includes administering an expression vector which includes a transcription unit encoding a secretable fusion protein that contains a DHFV antigen associated and CD40 ligand. A fusion protein that encodes a DHFV antigen associated with the virus and CD40 ligand may also be administered before, concurrently or after administration of the vector. Preferably, the fusion protein is administered after the vector. In this approach, the DHFV antigen which is encoded by the vector is chosen to cross-react with the DHFV virus for which protection is being sought.

In preferred embodiments, the expression vector may be a viral expression vector or a non-viral expression vector; the expression vector may be an adenoviral vector; the vector may be advantageously administered subcutaneously; the vector may be administered on a subsequent occasion(s) to increase the immune response; a signal sequence may be placed upstream of the fusion protein for secretion of the fusion protein; immunity against the antigen may be long lasting and involve generation of cytotoxic $CD8^+$ T cells against antigen expressing cells and the production of antibody to the antigen; the transcription unit may include sequence that encodes a linker between the DHFV antigen and the CD40 ligand; suitable linkers may vary in length and composition; the expression vector may include a human cytomegalovirus promoter/enhancer for controlling transcription of the transcription unit; and the CD40 ligand may be a human CD40 ligand.

Methods to chemically couple one protein to another (carrier) protein are well known in the art and include, for example, conjugation by a water soluble carbodiimide such as 1-ethyl-3-(3dimethylaminopropyl) carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate and, conjugation with gluteraldehyde (see, for example, reference 40; see, also, U.S. Pat. Nos. 4,608,251 and 4,161,519).

The term "vector" which contains a transcription unit (aka. "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110, 744; 6,133,029.

As used herein, the term "cells" is used expansively to encompass any living cells such as mammalian cells, plant cells, eukaryotic cells, prokaryotic cells, and the like.

The term "adenoviral expression vector" as used herein, refers to any vector from an adenovirus that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

"Adenoviral expression vectors" may include vectors that have been modified to better target and infect specific cell types (e.g., fibroblasts and dendritic cells), or that have been modified to avoid neutralization by pre-existing, high-titer antibodies, such as the antibodies circulating in humans against Ad5 and Ad2.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3,' a secretory signal sequence, a DHFV antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (aka. "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous tumor antigen signal sequence also may be used to direct secretion.

As is well known in the art, an antigen may be protein in nature, carbohydrate in nature, lipid in nature, or nucleic acid in nature, or combinations of these biomolecules. As is well known in the art, an antigen may be native, recombinant or synthetic. For example, an antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

Applicant selected the E protein of DHFV for the target of our vaccine since in the flavivirus group, to which DHFV belongs, the E protein is one of the major targets for neutralizing antibodies (5, 36-37). The E protein is therefore thought to be necessary for attachment of the virus to host cells, and for the low pH fusion of the host cell membranes with the virus which is necessary for viral entry into cells (36-37).

The general criteria utilized for selecting fragments of the E protein, which when attached to the aminoterminal end of the ecdCD40L, can generate a neutralizing antibody immune response are as follows:
1. To prevent a DHFV infection by generating high levels of E protein specific neutralizing antibodies to DHFV, the fragment must have the ability to be recognized and bound by Class II MHC and occupy a region in the DHVF antigen needed for infection of cells by DHFV.
2. To prevent or reduce the probability of escape from the negative selective pressure of the immunological response due to sequence evolution of regions of the E protein selected for the vaccine by attaching 3 fragments of Domain III of each strain of the E protein (amino acids 294-320, amino acids 321-354. and amino acids 355-395), where each fragment is separately attached to the aminoterminal end of the ecdCD40L.
3. To prevent the destabilization of the homotrimeric structure of the ecdCD40L from the attachment of the TAA to the aminoterminal end of the ecdCD40L, the fragments of the E protein will be chosen such that the molecular weight of the combined TAA is not too big.
4. While three fragments of Domain III have been selected for each of the four strains as a preferred embodiment, one could select, for example, four or more fragments of Domain III of each strain of the E protein.

The vaccine is a fusion protein comprised of a fragment taken from the E protein of DHFV, which is essential for the binding and uptake of the DHFV by monocytes and other cells of the human host (36-37), which is attached to the extracellular domain (ecd) of the CD40 ligand (CD40L). Three separate fragments of Domain III of E (ED) which are numbered $E_{294-320}$, $E_{321-355}$ and $E_{356-395}$ are chosen from Domain III of the E protein of the four different strains (SI, SII, SIII and SIV) of the DHFV (38). This generates 12 vaccines as shown below in Table I The invention consists of generating 12 different TAA/ecdCD40L vaccines as shown in Table I as a preferred embodiment. In Table 1, $E_{294-320}$, $E_{321-355}$ and $E_{356-395}$ refer to the fragment of Domain III of the E protein which is attached to the ecdCD40L. In addition, the Roman numeral that follows the "S" (I, II, III and IV) under the "Vaccine" column, refers to the strain of DHFV from which the E protein fragment comes.

TABLE 1

| Vaccines for DHFV | | | | |
|---|---|---|---|---|
| E Protein Fragment | Strain of DHFV | | | |
| Vaccine | I | II | III | IV |
| 1. $E_{294-320}$SI/ecdCD40L | X | | | |
| 2. $E_{294-320}$SII/ecdCD40L | | X | | |
| 3. $E_{294-320}$SIII/ecdCD40L | | | X | |
| 4. $E_{294-320}$SIV/ecdCD40L | | | | X |
| 5. $E_{321-355}$SI/ecdCD40L | X | | | |
| 6. $E_{321-355}$SII/ecdCD40L | | X | | |
| 7. $E_{321-355}$SIII/ecdCD40L | | | X | |
| 8. $E_{321-355}$SIV/ecdCD40L | | | | X |
| 9. $E_{356-395}$SI/ecdCD40L | X | | | |
| 10. $E_{356-395}$SII/ecdCD40L | | X | | |
| 11. $E_{356-395}$SIII/ecdCD40L | | | X | |
| 12. $E_{356-395}$SIV/ecdCD40L | | | | X |

The amino acid sequences of the fragments of the E protein from each Dengue strain are given below. These are derived from FIG. 3 of Sukupolvi-Petty et al, (38).
1. $E_{294-320}$ Fragment from Strain I:
LKGMSYVMCTGSFKLEKEVAETQHGTV (SEQ ID #1)
2. $E_{294-320}$ Fragment from Strain II:
LKGMSYSMCTGKFKVVKEIAETQHGTI (SEQ ID#2)
3. $E_{294-320}$ Fragment from Strain III:
LKGMSYAMCLSSFVLKKEVSETQHGTI (SEQ ID#3)
4. $E_{294-320}$ Fragment from Strain IV:
IKGMSYTMCSGKFSIDKEMAETQHGTT (SEQ ID #4)
5. $E_{321-355}$ Fragment from Strain I:
LVQVKYEGTDAPCKIPFSTQDEKGATQMGRLITA (SEQ ID #5)
6. $E_{321-355}$ Fragment from Strain II:
VIRVQYEGTGSPCKIPFEIMDLEKRHVLGRLITV (SEQ ID #6)
7. $E_{321-355}$ Fragment from Strain III:
LIKVEYKGEDAPCKIPFSTEDGQGKAHNGRLITA (SEQ ID #7)
8. $E_{321-355}$ Fragment from Strain IV:
VVKVKYEGAGAPCKVPIEIRDVNKEKVVGRIISS (SEQ ID #8)
9. $E_{356-395}$ Fragment from Strain I:
NPIVTDKEKPVNIEAEPPFGESYIVVGAGEKA-LKLSWFKK (SEQ ID #9)
10. $E_{356-395}$ Fragment from Strain II:
NPIVTEKDSPVNIEAEPPFGDSYIIIGVEPGQLKN-WFKK (SEQ ID #10)
11. $E_{356-395}$ Fragment from Strain III:
NPVVTKKEEPVNIEAEPPFGESNIVIGIGDKALKIN-WYKK (SEQ ID #11)
12. $E_{356-395}$ Fragment from Strain IV:
TPLAENTNSATNIELEPPFGDSYIVIGVGNSALTLHW-FRK (SEQ ID #12)

For example, the first vaccine listing under the "Vaccine" column, is $E_{294-320}SI/ecdCD40L$, when read across the column on a horizontal basis, connotes that it applies to the $E_{294-320}$ fragment of Domain III of the E Protein and to Strain I of the DHFV.

This mixture of these 12 vaccines (listed under the "Vaccine" column), can make the weak DHFV antigens potent immunogens, overcome the defective response in immunodeficient individuals, and induce an immune response to all VHF strains simultaneously. The vaccines in Table 1 could refer to transcription units in DNA plasmid, adenoviral vectors, or to the E/ecdCD40L fusion protein itself. In addition, the vaccine could be a combination of vector prime and protein boosts. Both the vector prime and protein boost are comprised of mixtures of 12 different vaccines (adenoviral vector or protein boost). If a plasmid vaccine is used, then mixtures of the 12 types of vaccine shown in Table 1 would be used.

The attachment of fragments of Domain III of the DHFV E protein to the ecdCD40L (E/ecdCD40L) would increase the potency of the E antigens from all 4 strains of DHFV as immunogens, thereby overcoming the more important factors which limit current vaccines for DHFV. The attachment of the E antigens to the ecdCD40L would make weak antigens more potent immunogens. The E/ecdCD40L vaccine would promote presentation of the E antigenic peptides on Class II MHC on DCs. Moreover, the administration of E/ecdCD40L vaccines, which contain fragments of domains of each of the three domains of the E protein for all 4 DHFV viral strains would induce high titer, fully protective neutralizing antibodies simultaneously to all four strains of the DHFV. This would prevent what is a major problem: immunological escape for heterologous strains and increased susceptibility to heterologous strains of the DHFV following the weak immune response to an initial vaccination or infection with a single strain.

These 12 vaccines are delivered as a mixture and administered subcutaneously. The vaccine can be delivered as a mixture of the fusion proteins. Alternatively, the vaccine can be delivered as a mixture of 12 adenoviral expression vectors. Alternatively, the vaccine can be delivered as a mixture of 12 plasmid DNA expression vectors.

Published Papers Relevant to the DHFV TAA/ecdCD40L Vaccine

1. Gubler D J. Epidemic dengue/dengue hemorrhagic fever as a public health social and economic problem in the 21$^{st}$ century. Trends Microbiol 10: 100-103, 2002.
2. WHO. Dengue: guidelines for diagnosis, treatment, prevention and control-new edition. Geneva: World Health Organization 2009. http://whqlibdoc.who.int/publications/2009/978924547871_eng.pdf(accessed Jul. 23, 2012).
3. Gubler D J. The economic burden of dengue. Am J Trop Med Hyg 86: 743-744, 2012.
4. Healty M E, Stone A, Fitzsimmons D W et al. Asia-Pacific and Americas Dengue Prevention Boards Surveillance Working Group. Best practices in dengue surveillance: a report from the Asia-Pacific and Americas Dengue Prevention Boards. PLoS Negl Trop Dis 4:e890, 2010.
5. Whitehead S S, Blaney J E, Durbin A P, and Murphy B R. Prospects for a dengue virus vaccine. Nature Reviews Microbiology 5: 518-528, 2007.
6. Zellwager R M, Prestwood T R, and Shresta S. Enhanced infection of liver sinusoidal endothelial cells in a mouse model of antibody-induced severe dengue disease. Cell Host & Microbe 7: 128-139, 2010.
7. Balsitis S J, Williams K L, Lachica R, et al. Lethal antibody enhancement of dengue disease in mice is prevented by Fc modification. PLos Pathogens 6: e10000790, 2010.
8. Beltramello M, Williams K L, Simmons C P et al. The human immune response to dengue virus is dominated by highly cross-reactive antibodies endowed with neutralizing and enhancing activity. Cell Host & Microbe 8: 271-283, 2010.
9. Simmons C P, Farrar J J, Nguyen v V et al. Dengue. N Engl J Med 366: 1423-1432, 2012.
10. Coller B A, and Clements D E. Dengue vaccines; progress and challenges. Curr Opin Immunol 23: 391-398, 2011.
11. Halstead S B. Dengue. Lancet 370: 1644-1652, 2007.
12. Bixler J. Florida confirms 24 cases of dengue fever in Key West. CNN, Aug. 3, 2010.
13. Chen H C, Hofman F M, Kung J T, LinYD, Wu-Hsieh B A. Both virus and tumor necrosis factor alpha are critical for endothelium damage in a mouse model of dengue virus-induced hemorrhage. J Virology 81: 5518-5526, 2007.
14. Laughlin C, Cassetti M C, Rothman A et al. Report of an NIAID workshop on dengue animal models. Vaccine 28: 4229-4234, 2010.
15. Bray M, Men R, and Lai C J. Monkeys immunized with intertypic chimeric dengue viruses are protected against wild-type virus challenge. J Viology 70: 4162-4166, 1996.
16. Yauch L E and Shresta S. Mouse models of dengue virus infection and disease. Antiviral Research 80: 87-93, 2008.
17. Halstead S B. Dengue vaccine development: a 75% solution. Lancet online Sep. 11, 2012 http://dx.doi.org/10.1016/S0140-6736(12)6151.0-4.
18. Sabchareon A, Wallase D, Sirivichayakul C et al. Protective efficacy of the recombinant, live-attenuated, CYD tetravalent dengue vaccine in Thai school children: a randomized controlled phase 2b trial. Lancet online Sep. 11, 2012. http://dx.doi.org/10.1016/S0140-6736(12) 61428-7.
19. Jefferson T et al. Efficacy and effect of influenza vaccines in the elderly. Lancet 264: 1165-1174, 2005.
20. Goodwin K, Vibou C, Simonsen L. Antibody response to influenza vaccination in the elderly: a quantitative review. Vaccine 24: 1159-1169, 2006.
21. Jackson M L, Nelson J C, Weiss N S et al. Influenza vaccination and risk of community acquired pneumonia in immunocompetent elderly people: a population based nested case control study. The Lancet 372: 398-405, 2008.
22. Simonsen L, Taylor R J. Mortality benefits of influenza vaccination in elderly people: an ongoing controversy. Lancet Infect Dis 7: 658-666, 2007, Kraus A A, Haymore L B et al. Dengue virus neutralization by human immune sera: role of envelope protein domain III-reactive antibody. Virology 392: 103-113, 2009.
23. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. Journal of General Virology 84: 1623-1628, 2003.
24. Eaton S M, Burns E M, Kusser K, Radall T D, and Haynes L. Age-related defects in CD4 T cell cognate helper function lead to reductions in humoral responses. J Exp Med 200: 1613-1622, 2004.
25. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. *PNAS,* 100: 15101-15106, 2003.
26. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. *Clin Cancer Res* 10: 7738-7746, 2004.
27. Tang, Y, Zhang, L, Yuan, J, Akbulut H, Maynard J, Linton P-J, and Deisseroth, A. Multistep process through which adenoviral vector vaccine overcomes anergy to tumor-associated antigens. *Blood,* 104: 2704-2713, 2004.
28. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. *Mol Cancer Ther* 5:1975-1985, 2006.
29. Tang Y C, Maynard J, Akbulut H, Fang X M, Zhang W W, Xia X Q, Koziol J, Linton P-J, and Deisseroth A. Vaccine which overcomes defects acquired during aging and cancer. *Journal of Immunology* 177:5697-5707, 2006.
30. Tang Y, Akbulut H, Maynard J, Zhang L, Petersen L, and Deisseroth A. Vaccine strategies for cancer and infectious diseases in the elderly. *Gene Therapy,* Eds. Takenori Ochiai, Hideaki Shimada, and Masatoshi Tagawa, Published by Japanese Ministry of Education and Science, pp. 78-85, 2007.
31. Akbulut H, Akbulut K G, Tang Y C, Maynard J and Deisseroth A. Chemotherapy Targeted to Cancer Tissue Potentiates Antigen Specific Immune Response Induced by Vaccine for In Vivo Antigen Loading and Activation of Dendritic Cells. *Molecular Therapy,* 10:1753-1760, 2008.
32. Tang, Y C, Linton, P J, Thoman, M, and Deisseroth A. Symposium in Writing: Vaccine for Infections and Cancer. *Cancer Immunology and Immunotherapy,* 58: 1949-1957, 2009.
33. Han T H, Tang, Y C, Park Y H, Petersen L, Maynard J, Li P C, and Deisseroth A. Ad-sig-BcrAbl/ecdCD40L Vector Prime-BcrAbl/ecdCD40L Protein Boost Vaccine for P210Bcr-Abl Protein, In Press, Bone Marrow Transplantation, 2009. Tang, Y C, Linton, P J, Thoman M, and Deisseroth A. Symposium in Writing: Vaccine for Infections and Cancer. *Bone Marrow Transplantation,* 45: 550-557, 2010.
34. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. *Gene Therapy,* 17: 1333-1340, 2010.
35. Deisseroth A, Tang Y, Zhang L, Akbulut H, and Habib N. TAA/ecdCD40L adenoviral prime-protein boost vaccine for cancer and infectious disease. Cancer Gene Therapy 20: 65-69, 2013.
36. Wahala W M P B, Kraus A A, and Haymore L B. Dengue virus neutralization by human immune sera: role of envelope protein domain III-reactive antibody. Virology 392: 103-113, 2009.
37. Crill W E D and Roehrig J T. Monoclonal antibodies that bind to domain III of dengue virus E glycoprotein are the most-efficient blockers of virus adsorption to Vero cells. J Virology 75: 7769-7775, 2001.
38. Sukupolvi-Petty, S, Austin S K, Purtha W E, Oliphant T, Nybakken G E, Schlesinger J J, Roehrig J T, Gromowski G D, Barrett A D, Fremont D H, and Diamond M S. Type- and subcomplex-specific neutralizing antibodies against Domain III of Dengue virus type 2 envelope protein recognize adjacent epitopes. Journal of Virology 81: 12816-12826, 2007.

The invention claimed is:

1. A composition for generating a humoral and cellular immune response in an individual against four strains of the Dengue Hemorrhagic Fever Virus (DHFV) with the E antigenic protein of the DHFV, in the form of a multi expression vector mixture comprising twelve expression vectors each of which comprises an effective amount of a nucleic acid encoding a secretable fusion protein comprising one of twelve distinct epitopes SEQ ID NOS. 1-12 from Domain III of the E protein, wherein said twelve distinct epitopes comprise three separate fragments from each of said four strains, each of said twelve epitopes recognized and bound by Class I and Class II MHC capable to generate both neutralizing antibodies and CD8 effector T cells, and wherein each of said twelve epitopes is separately linked to the N-terminal end of the extracellular domain of a CD40 ligand to define one of twelve distinct sub-compositions, and to collectively define said multi-expression vector mixture composition that is potent to anticipate immunological escape to heterologous strains of the DHFV thereby providing protection against related but not identical DHFV viruses.

2. The composition of claim 1, wherein said neutralizing antibodies titers against the DHFV virus block the binding of the DHFV virus to cellular receptors and wherein each of said DHFV twelve epitopes is of a molecular weight and size that does not disrupt the assembly of a CD40L homotrimer.

3. The composition of claim 1, wherein a plasmid is employed instead of said expression vector.

4. A method of generating an immune response in an individual against Dengue Hemorrhagic Fever Virus (DHFV), by administering to the individual an effective amount of the composition of claim 1.

* * * * *